United States Patent
Mackie et al.

(10) Patent No.: US 7,120,354 B2
(45) Date of Patent: Oct. 10, 2006

(54) GASES DELIVERY CONDUIT

(75) Inventors: Scott Robert Mackie, Auckland (NZ);
Craig Karl White, Auckland (NZ);
Brett John Huddart, Auckland (NZ);
Daniel John Smith, Auckland (NZ);
Hussein Kadhum, Auckland (NZ);
Malcolm David Smith, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 10/270,805

(22) Filed: Oct. 15, 2002

(65) Prior Publication Data

US 2003/0059213 A1  Mar. 27, 2003

Related U.S. Application Data

(63) Continuation-in-part of application No. 09/956,723, filed on Sep. 20, 2001, which is a continuation-in-part of application No. 09/808,567, filed on Mar. 14, 2001.

(30) Foreign Application Priority Data

| Mar. 21, 2000 | (NZ) | ................................ | 503495 |
| Oct. 15, 2001 | (NZ) | ....................... | PCT/NZ01/00226 |
| Dec. 21, 2001 | (NZ) | ................................ | 516387 |
| Aug. 26, 2002 | (NZ) | ................................ | 521017 |

(51) Int. Cl.
*F24H 1/10* (2006.01)

(52) U.S. Cl. .................................. 392/480; 219/502
(58) Field of Classification Search ............... 392/472, 392/465, 466, 480; 219/502
See application file for complete search history.

(56) References Cited

U.S. PATENT DOCUMENTS

| 485,127 A | 10/1892 | Lynch |
| 3,582,968 A | 6/1971 | Buiting |
| 3,584,193 A | 6/1971 | Badertscher |
| 3,695,267 A | 10/1972 | Hirtz et al. |
| 3,766,914 A | 10/1973 | Jacobs |
| 3,914,349 A | 10/1975 | Stipanuk |
| 4,013,122 A | 3/1977 | Long |

(Continued)

FOREIGN PATENT DOCUMENTS

| DE | 3311811 | 10/1983 |

(Continued)

*Primary Examiner*—Thor S. Campbell
(74) *Attorney, Agent, or Firm*—Trexler, Bushnell, Giangiorgi, Blackstone & Marr, Ltd.

(57) ABSTRACT

A gases delivery conduit for the supply of humidified medical gases as formed from an extruded plastic tube. The extruded plastic tube includes at least one heating element embedded within the wall of the tube. The heating element includes a pair of electrical conductors separated by a positive temperature coefficient material wherein the localised resistance of the material is positively related to the localised temperature.

19 Claims, 5 Drawing Sheets

U.S. PATENT DOCUMENTS

| | | |
|---|---|---|
| 4,013,742 A | 3/1977 | Lang |
| 4,038,980 A | 8/1977 | Fodor |
| 4,060,576 A | 11/1977 | Grant |
| 4,110,419 A | 8/1978 | Miller |
| 4,172,105 A | 10/1979 | Miller et al. |
| 4,500,480 A | 2/1985 | Cambio, Jr. |
| 4,574,188 A | 3/1986 | Midgley et al. |
| 4,640,804 A | 2/1987 | Mizoguchi |
| 4,676,237 A | 6/1987 | Wood et al. |
| 4,684,786 A | 8/1987 | Mann et al. |
| 4,710,887 A | 12/1987 | Ho |
| 4,722,334 A | 2/1988 | Blackmer et al. |
| 4,753,758 A | 6/1988 | Miller |
| 4,780,247 A | 10/1988 | Yasuda |
| 4,829,998 A | 5/1989 | Jackson |
| 4,911,157 A | 3/1990 | Miller |
| 4,911,357 A | 3/1990 | Kitamura |
| 4,941,469 A | 7/1990 | Adahan |
| 5,031,612 A | 7/1991 | Clementi |
| 5,062,145 A | 10/1991 | Zwaan et al. |
| 5,092,326 A | 3/1992 | Winn et al. |
| 5,101,820 A | 4/1992 | Christopher |
| 5,148,801 A | 9/1992 | Douwens et al. |
| 5,224,923 A | 7/1993 | Moffett et al. |
| 5,336,156 A | 8/1994 | Miller et al. |
| 5,346,128 A | 9/1994 | Wacker |
| 5,367,604 A | 11/1994 | Murray |
| 5,388,443 A | 2/1995 | Manaka |
| 5,392,770 A | 2/1995 | Clawson et al. |
| 5,404,729 A | 4/1995 | Matsuoka et al. |
| 5,454,061 A | 9/1995 | Carlson |
| 5,482,031 A | 1/1996 | Lambert |
| 5,529,060 A | 6/1996 | Salmon et al. |
| 5,558,084 A | 9/1996 | Daniell et al. |
| 5,564,415 A | 10/1996 | Dobson et al. |
| 5,588,423 A | 12/1996 | Smith |
| 5,640,951 A * | 6/1997 | Huddart et al. ........ 128/204.17 |
| 5,673,687 A | 10/1997 | Dobson et al. |
| 5,759,149 A | 6/1998 | Goldberg et al. |
| 5,769,071 A | 6/1998 | Turnbull |
| 5,988,164 A | 11/1999 | Paluch |
| 6,024,694 A | 2/2000 | Goldberg et al. |
| 6,050,260 A | 4/2000 | Daniell et al. |
| 6,078,730 A | 6/2000 | Huddart et al. |
| 6,095,505 A | 8/2000 | Miller |
| 6,125,847 A | 10/2000 | Lin |
| 6,158,431 A | 12/2000 | Poole |
| 6,311,958 B1 | 11/2001 | Stanek |
| 6,349,722 B1 | 2/2002 | Gradon et al. |
| 6,367,472 B1 | 4/2002 | Koch |
| 6,394,084 B1 | 5/2002 | Nitta |
| 6,397,846 B1 | 6/2002 | Skog et al. |
| 6,463,925 B1 | 10/2002 | Nuckols et al. |
| 6,474,335 B1 | 11/2002 | Lammers |
| 6,543,412 B1 | 4/2003 | Amou et al. |
| 6,564,011 B1 * | 5/2003 | Janoff et al. ................. 392/480 |
| 6,694,974 B1 | 2/2004 | George-Gradon et al. |
| 2002/0124847 A1 | 9/2002 | Smith et al. |

FOREIGN PATENT DOCUMENTS

| | | |
|---|---|---|
| DE | 3311811 | 10/1984 |
| DE | 3629353 | 1/1988 |
| DE | 4034611 | 5/1992 |
| DE | 94092311 | 11/1994 |
| EP | 0258928 | 9/1988 |
| EP | 481459 | 4/1992 |
| EP | 556561 | 8/1993 |
| EP | 0672430 | 9/1995 |
| EP | 0885623 | 12/1998 |
| EP | 1138341 | 10/2001 |
| EP | 0556561 | 8/2003 |
| GB | 1167551 | 10/1969 |
| GB | 2277689 | 11/1994 |
| JP | 0 5317428 | 12/1993 |
| JP | 08061731 | 8/1996 |
| JP | 0 9234247 | 9/1997 |
| JP | 09234247 | 9/1997 |
| SU | 379270 | 4/1973 |
| WO | WO 9826826 | 6/1998 |
| WO | WO0110489 | 2/2001 |
| WO | WO 02/32486 | 4/2002 |
| WO | WO 02/32486 | 4/2003 |

* cited by examiner

GASES DELIVERY CONDUIT

This is a continuation-in-part patent application of U.S. patent application Ser. No. 09/956,723 filed on Sep. 20, 2001 (pending) which is a continuation-in-part application of U.S. patent application Ser. No. 09/808,567 (pending) filed on Mar. 14, 2001.

BACKGROUND TO THE INVENTION

1. Field of the Invention

The present invention relates to conduits for the delivery of gases, and in particular to conduits for the delivery of gases to patients in a medical environment.

2. Summary of the Prior Art

Many methods are known in the art for supplying humidified gases to a patient requiring breathing assistance. It is known in the art to provide a heater to minimise condensation on the internal surfaces of the conduit. In that regard it is known to provide a plain or coiled heater wire within the lumen of the conduit, such an embodiment being illustrated in for example U.S. Pat. No. 6,078,730. In this case the heater wire is disposed within the gases flow and maintain the temperature of the gases flow to reduce condensation. It is also known to provide a heater wire on the conduit, for example disposed helically on the outer wall of the conduit as in U.S. Pat. No. 5,454,061. This heats the conduit wall, to in turn heat the gases flowing through the lumen of the conduit.

While these heated wall conduits are reasonably effective there is still room for improvement. Furthermore, the forming method involves winding the conduit from a thin narrow tape applied to a mandrel with adjacent turns overlapping. This forming method is comparatively slow, making these conduits expensive to manufacture.

SUMMARY OF THE INVENTION

It is therefore an object of the present invention to provide a gases conduit which goes some way to overcoming the above mentioned disadvantages, or which will at least provide a useful choice.

In a first aspect the invention consists in a gases delivery conduit for the supply of humidified medical gases, said conduit comprising:

an extruded plastic tube, and at least one heating element embedded within the wall of the tube to be partially or wholly contained within said wall, said heater element including a pair of electrical conductors separated by a positive temperature coefficient ("PTC") material wherein the localised resistance of said material is positively related to the localised temperature.

Preferably the cross sectional profile of said extruded plastic tube includes inwardly extending ribs on its inner surface, such that total collapse or total occlusion is not possible during bending.

Preferably the heating element is embedded within the inwardly extending internal ribs of the tube.

Said heating element may be an elongate flattened tape at least as long as the tube, and having a width and a thickness, with said width being greater than said thickness.

Said tape may include a said conductor disposed along each of a pair of side edges, with a web of said PTC material spanning between said conductors.

Alternatively said tape may include an elongate flattened ribbon of said PTC material with a first face and a second face, a said conductor is distributed over said first face, and another said conductor is distributed over said second face.

Preferably the heating element is spiralled or braided within the tube wall.

Preferably said conduit includes a connector at each end, at least one said connector having one or more electrical contacts contacting and connecting with one or more of the conductors of said heating elements, said connector having an external connection interface and an electrical connection between each said contact and said external connection interface.

Preferably said connector with said external connection interface has a gases port configured to make a connection with a mating gases port in a first direction, and said connection interface is configured to make connection with a mating connection interface also in said first direction.

Preferably said positive temperature coefficient material has a phase transformation temperature between 28° C. and 45° C.

In a further aspect the present invention consists in a method of manufacturing a conduit for the supply of humidified medical gases comprising:

preparing at least one elongate heating element including a pair of electrical conductors separated by a positive temperature coefficient ("PTC") material wherein the localised resistance of said material is positively related to the localised temperature, extruding a plastic tube and simultaneously drawing said heating element into the melt of the extruded tube such that the element is embedded within the wall of the tube and captured as the melt solidifies.

Preferably said method includes spiralling the heating elements within the tube wall by twisting the extruded tube during forming.

Alternatively said method includes moving the points where the heating elements enter the melt of the extruded tube to spiral or braid the heating elements within the tube wall.

Preferably said method includes in a continuous process:
extruding an inner tube layer,
applying said elongate heating element to an outer face of said inner tube layer, and
extruding an over tube layer over said inner tube layer to encapsulate said elongate heating element between said inner layer and said outer layer.

Preferably said method includes the further steps of:
(a) removing tube material to expose conductors of the heating elements; and
(b) sliding a circular connector over the trimmed and untrimmed section of the conduit to completely cover the exposed conductors, said circular connector including at least one electrical contact on its inner surface, which thereby comes into contact with said exposed conductors.

Preferably said method includes between steps (a) and (b), the further step of:
bending back one of the exposed conductors of said heating element over the untrimmed section of said tube;
and wherein at step (b) said circular connector includes at least a pair of contacts on its inner surface, with a said contact arranged to contact the bent back conductor of said heating element and another said contact arranged to contact the other conductor of said heating element.

In a yet further aspect the invention consists in a method of terminating an extruded plastic tube with an embedded heating element, the heating element including a pair of electrical conductors separated by a positive temperature coefficient ("PTC") material wherein the localised resistance of said material is positively related to the localised temperature, the method comprising the steps of:

(a) removing tube material to expose conductors of the heating element, and
(b) sliding a circular connector over the trimmed and untrimmed section of the conduit to completely cover the exposed conductors, said circular connector including at least one electrical contact on its inner surface, which thereby come
into contact with said exposed conductors.

Preferably said method includes between steps (a) and (b), the further step of: bending back one of the exposed conductors of said heating element over the untrimmed section of said tube;

and wherein at step (b) said circular connector includes at least a pair of contacts on its inner surface, with a said contact arranged to contact the bent back conductor of said heating element and another said contact arranged to contact the other conductor of said heating element.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

FIGS. 8A to 8E illustrate a method of terminating a tube according to embodiments of the present invention. In particular

DETAILED DESCRIPTION OF THE PREFERRED EMBODIMENTS

The present invention provides a conduit with heating elements embedded within the tubing walls.

Figure 1:
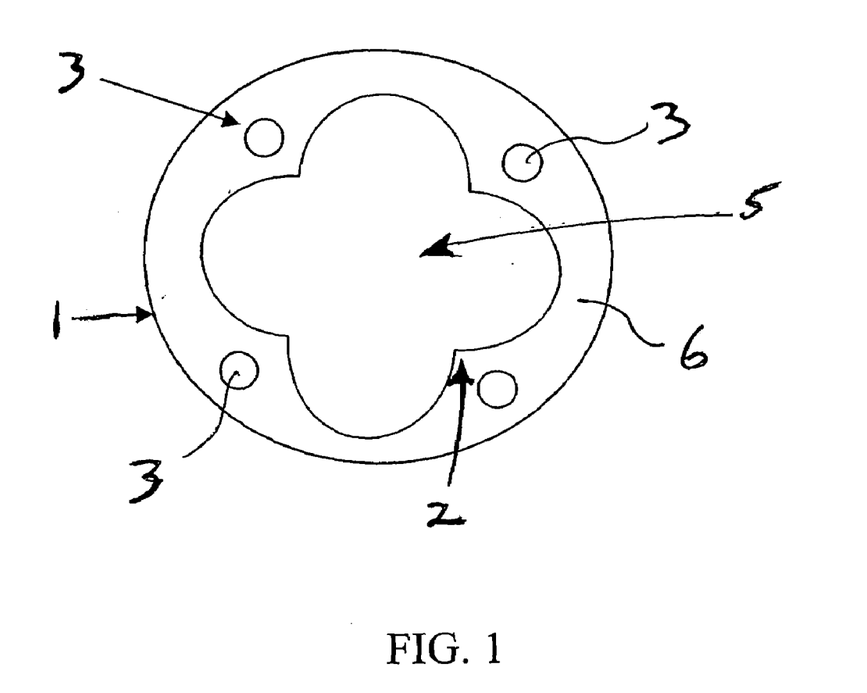
FIG. 1 is a cross section of a tube according to a preferred embodiment of the present invention.

Referring to FIG. 1, according to a preferred embodiment of the invention the conduit 1 is extruded from an appropriate plastics material, such as a flexible polymer, suitable for use in healthcare products and being electrically insulative. The conduit has ridges or ribs 2 extending from the surface of the conduit wall 6. Each rib extends towards the centre of the conduit and has heating element 3 embedded in it along the conduit's length. The heater element 3 is an electrical resistance heater exhibiting a positive temperature coefficient behaviour, wherein the localised resistance of said material is positively related to the localised temperature. The heater wire is embedded within the ribs of the conduit by co-extrusion at the time the polymer conduit is extruded.

Although FIG. 1 shows a conduit with four ribs on the inner wall, the conduit may be provided with any number of ribs that is practical. Also, the number of heating elements may not correspond with the number of ribs provided in the conduit inner wall. Additional heating elements may be embedded in the conduit skin between ribs, multiple heating elements may be provided in a rib, or some ribs may be provided without heating elements. The number (density) of heating elements will depend on the heating requirements and application of the tube.

A conduit in this embodiment enables the gases flowing through the centre 5 of the conduit to be heated, maintaining an appropriate moisture content and temperature. Furthermore, the ribs 2 provide the added advantage that if the conduit is pressed, crushed or bent the ribs prevent total occlusion of the conduit.

The heater element of the present invention is formed including a positive temperature coefficient (PTC) material.

The resistance of a PTC material increases markedly once it reaches a threshold temperature, resulting in reduced power consumption and subsequent cooling. The delivery tube may pass through more than one environment, or may have localised drafts present on certain parts of the tube.

In the present invention the PTC heater is provided as an elongate structure embedded in the wall of the delivery tube. The construction of the PTC heater according to one embodiment is illustrated in to FIG. 2. In particular the heater structure is formed as a tape from a ribbon 20 of PTC plastic material with conductors 21, 22 embedded in the plastic material adjacent the opposite edges thereof. In use the conductors are attached to a power supply to provide a voltage difference between the conductors and cause a current to flow between them depending on the resistance of the PTC material.

Figure 2:
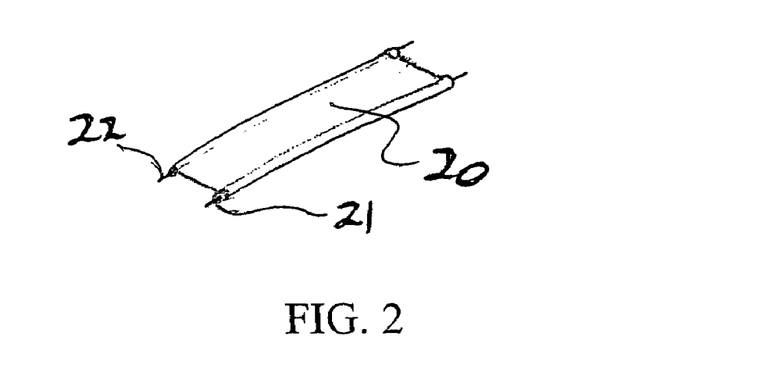
FIG. 2 is a plan view of a section of a ribbon of PTC material with an electrode embedded along each edge.

The tape may be provided in the tube wall as lengths of tape blindly terminated at one end and terminated with a power connector at the other end. The blind termination is without connection between the conductors. Preferably it is simply that the ribbon is cut off where the conduit is cut off.

Where multiple lengths of tape are provided in the tube wall the power connector connects the first terminal with one wire of each ribbon and a second terminal with the other wire of each ribbon.

With the pair of conductors provided along opposite edges of the ribbon the PTC material offers an amorphous array of parallel current paths along the entire length of the ribbon. Where the conduit temperature is lower the heater structure will have a lower resistance and more current will flow producing a greater heater effect. Where the conduit temperature is higher the PTC material will have a higher resistance, choking off current flow and reducing heating in that region of the conduit.

Figure 4:
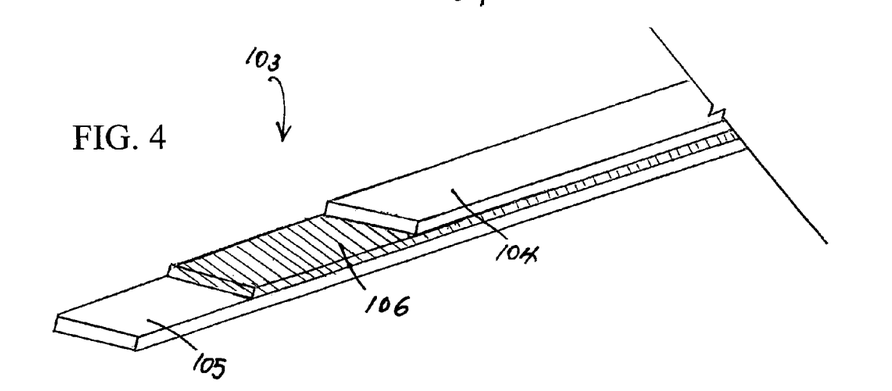
FIG. 4 shows an alternative construction of a tape form of PTC heating element.

Referring now to FIG. 4 in an alternative form the PTC heating element may be a layered tape 103. The tape 103 is made up from at least two conductor layers 104, 105 and an intermediary PTC material layer 106. The laminate of conductive layers and PTC layer is held together by natural adhesion, but if necessary additional conductive adhesive layers could be used to bond the laminated layers together. Particularly, during the forming of the conductive tape the PTC layer is preferably in a molten form and is allowed to flow between the conductive layers to form the laminated film. Other forms of manufacture, such as placing a PTC sheet between conductive sheets and heating the film so that the layers bond together, are possible.

The laminate may be formed in wide sheets, rolled up and cut into narrow rolls of tape.

Alternatively the laminated tape may be formed directly in its narrow state. In the preferred form the conductive layers 104, 105 are thin and narrow sections or sheets of copper, copper alloy or other appropriate electricity conducting material.

Figures 7, 8A:
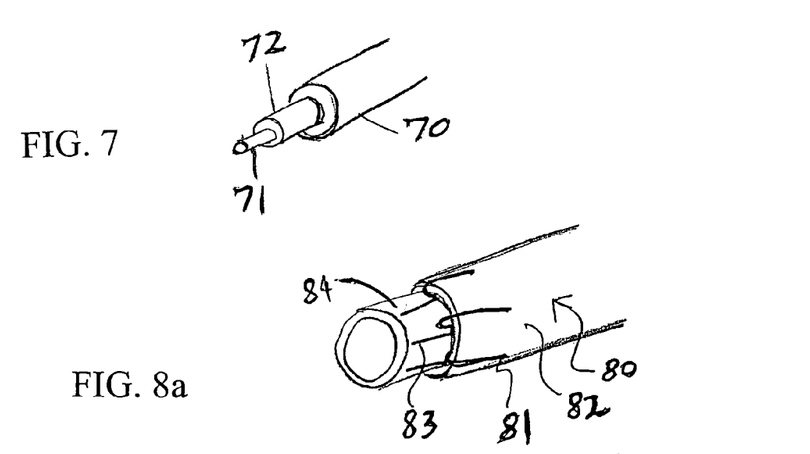
FIG. 7 shows construction of a wire form PTC heating element.
FIG. 8A is a perspective view of one end of a conduit, with an outer layer of the tube removed and a conductor of each heater element turned back over the remaining outer portion of the tube.

With reference to FIG. 7 the discrete PTC heating element may be formed as a wire rather than a ribbon, including an outer electrode 70, and an inner electrode 71 and an intermediate layer 72 of PTC material.

Figure 3:
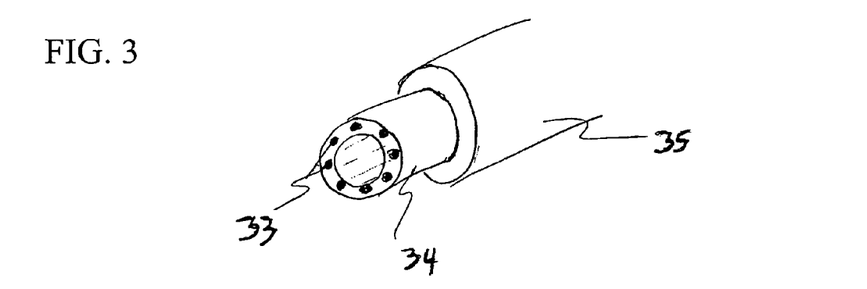
FIG. 3 is a perspective view with cutaway of a multilayer tube, with layers having different properties.

An additional embodiment of the present invention is illustrated in FIG. 3, in which the heater elements 33 are disposed within the tube wall and the tube wall is composed of multiple layers 34 and 35 of extruded material, adjacent layers having differing properties. The multiple layers of material are preferably co-extruded concentrically. FIG. 3 illustrates an example of such a conduit with the outer layer 35 cut away to reveal inner layer 34. Desirable property combinations in a heated tube would comprise, by way of example, the inner layer 34, containing the heater elements, being of a tough, heat transmissive plastic material and the outer layer being for example a foamed or open cell or otherwise insulative plastic material. An additional inner surface layer might be provided with anti-condensate properties. Alternatively a wicking layer, for example a foam plastic layer, may be provided on the inner surface to entrain any collected water for re-evaporation.

Figure 5:
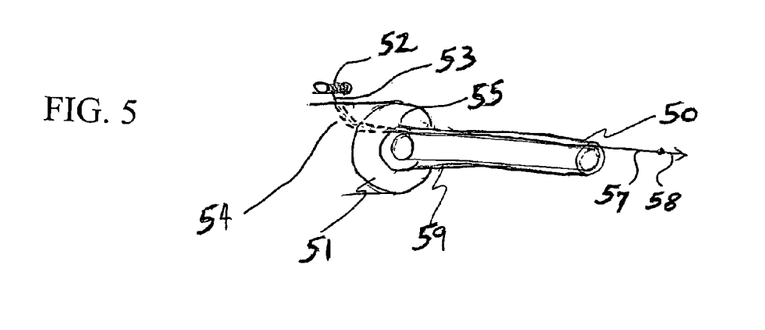
FIG. 5 is a perspective view with cut away and hidden detail showing a tube being extruded from a extrusion die with a wire drawing passage into the die.

A method of extruding a tube according to the present invention is described with reference to FIG. 5. According to this method a tube 50 is extruded from a die 51 in a normal manner. Simultaneously a heating element 53 is drawn into the tube wall, passing from a spool 52 through a passage 54 exiting into the extrusion melt adjacent the die outlet 55, but preferably there within. The molten tube 59 solidifies, encapsulating the heating element 53. The heating element 53 may be used to provide assistance in the extrusion process, with a tension force 58 being applied to the free end 57, helping to draw the heating element into the extrusion melt and support the formed conduit. FIG. 5 illustrates the invention in respect of only a single element being drawn in the melt. Clearly in all practical embodiments more than one heating element will be simultaneously drawn in this manner, with the extrusion die including multiple element conducting passages.

Figure 6A:
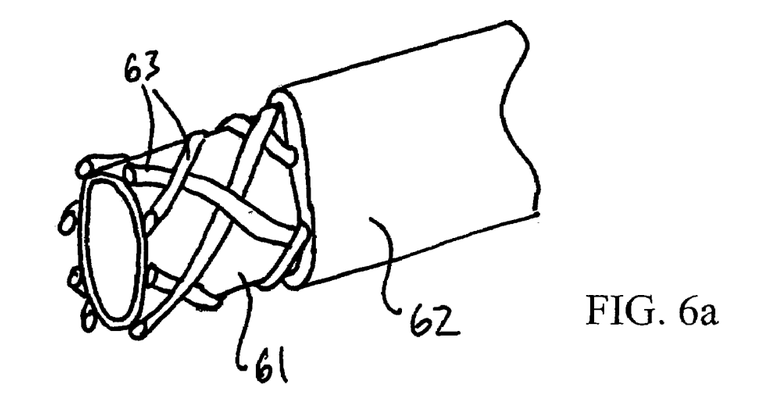
FIG. 6A is a perspective view of a section of conduit with multiple heating elements braided into the tube wall.
Figure 6B:
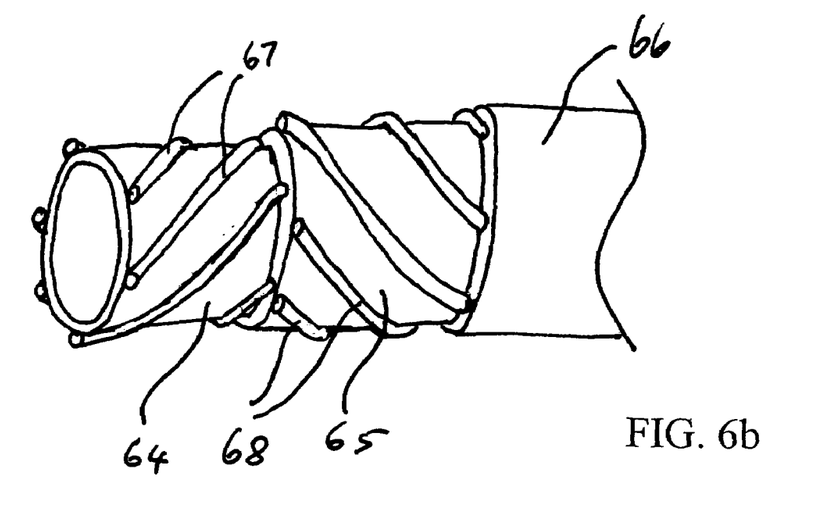
FIG. 6B is a perspective view of a section of conduit with multiple heating elements spirally embedded in the tube wall.

Referring to FIGS. 6A and 6B it may be desirable to provide braided or spirally embedded elements in the tube wall. This may be achieved by having a rotating portion of the extrusion die carrying the element spools and passages, or more simply by providing one or more rotating spool carrying heads around the molten portion 59 of the extruded conduit.

Rather than embedding wires into the molten outer surface of the conduit, the conduit may be extruded sequentially as a series of layers with the wires provided on the outer surface of a layer before the next outward layer is extruded over them. In this way elements may be provided over an extruded inner tube layer using a rotating braider through which the extruded tube layer is passed longitudinally. An outer tube layer is subsequently extruded over the inner tube and elements. An example of a resulting product is shown in FIG. 6A. the tube includes an inner plastic layer 61, an outer plastic layer 62 and braided heating element 63 embedded in the outer layer 62.

In the case of braiding heating elements will pass over and contact one another within the tube wall. Therefor it is necessary to guard against short-circuiting between heating elements. For example this method is more appropriate for the heating element of FIG. 7 where any contacting between elements will be between the outer electrode which will have common potential. Braiding may be appropriate for the element of FIG. 5 so long as the element is laid uniformly and the elements spiralling in one direction are inverted relative to the elements spiralling in the other direction. This ensures that any electrodes coming into contact have common polarity. The arrangement would probably not be appropriate for the heating element of FIG. 2 unless the lengths of heating element are electrically insulated from one another. Otherwise there is potential for a short-circuit to develop if the PTC material breaks down or wears where it separates conductors of opposite polarity.

Instead a conduit may be formed with separate spool carrying heads forming the spirals of each direction without any provision for the weaving effect produced by a braiding head. These heads may be provided with a cross head extruder between them providing an intervening layer of electrically insulating plastic material. A conduit in this way is illustrated in FIG. 6B. The conduit includes an inner layer 64, an electrically insulating middle layer 65, and an outer layer 66. A first set of spiralled heating elements 67 are interposed outside inner layer 64 and embedded in middle layer 65. A second set of spiralled heating elements 68 are interposed outside middle layer 65 and embedded in outer layer 66.

The tube according to the present invention may be terminated as appropriate to allow electrical connection of the element conductors as necessary according to the form of heating element used.

Figures 8B, 8C:
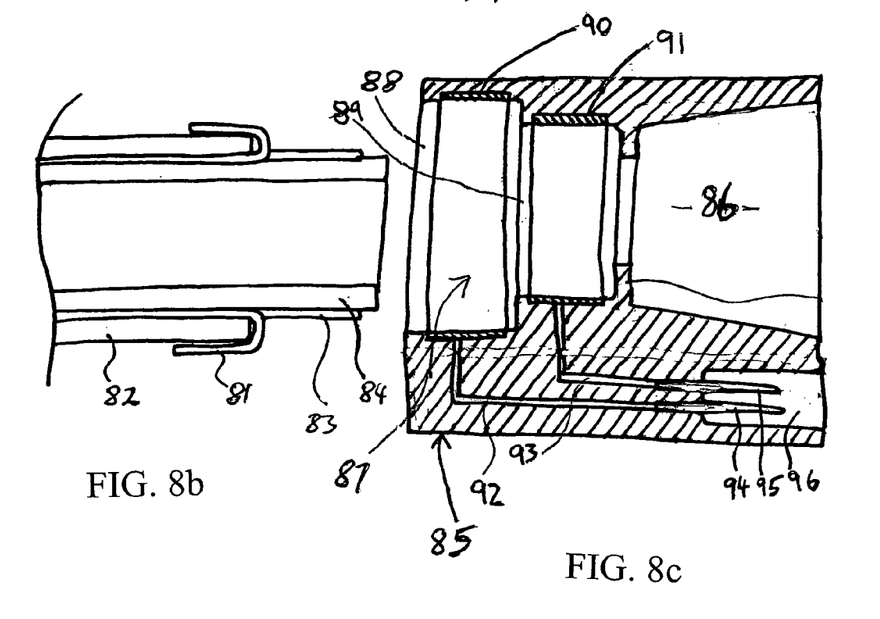
FIG. 8B is a cross sectional elevation of the end of FIG. 8A.
FIG. 8C is a cross sectional elevation of a conduit inlet connector.

One preferred method of termination is illustrated by the sequence of FIGS. 8A to 8E. In the first step of terminating the conduit the outer plastic layer 82 of the conduit 80 is trimmed back to expose the PTC heating elements. The pair of conductors embedded in the PTC heating elements are separated from the PTC material and exposed. A conductor 81 of each heating element is bent back over the outside surface of the tube 80. The other conductor 83 of each PTC heating element remains adjacent the outside surface of the projecting inner portion 84 of the tube 80. This arrangement is illustrated in FIGS. 8A and 8B.

A connector 85 is configured to fit over the trimmed and prepared end of conduit 80. The connector 85 has an open passage therethrough The open passage includes a gases port connection opening 86 at one end and a stepped cavity 87 at the other end. The stepped cavity 87 has inwardly facing cylindrical surfaces 88 and 89. Cylindrical surface 88 is of larger diameter than cylindrical surface 89. Surface 88 is sized to provide a slight interference fit over the outer most conductors 81 (turned back over the outside of conduit 80). The inner cylindrical surface 89 is sized to provide a slight interference fit over the exposed conductors 83 adjacent inner portion 84 of conduit 80. A first contact is provided embedded in the cylindrical surface 88 and a second contact is provided embedded in the cylindrical 89. The first contact is preferably in the form of an annular conductive ring 90 (for example of copper or other material having good surface conductivity). The second contact is preferably also an annular ring 91 of similar conductive material. The body of the connector is made from any suitable electrically insulating plastic material.

Electrical conductors are provided through the body of the connector 85 to allow an electrical connection to be made from the outside of the connector 85 to the first contact 90 and second contact 91. A conductor 92 is electrically connected to the first contact ring 90 and extends through the body of connector 85 to a connection pin 94. A conductor 93 is electrically connected with the second contact ring 91 and extends through the body of connector 85 and is electrically connected with a second pin 95. The conductors 92 and 93 may alternatively extend to be free of the body of connector 85 and be terminated for example with a plug or socket. However preferably the pins 94 and 95 are provided in an integral socket 96 on the connector 85. The socket 96 opens in the same direction as port 86. This allows for use of this particular connector in conjunction with appropriately configured gases supply equipment having a mutually configured plug portion adjacent its gases outlet port, so that electrical and pneumatic connections can be made simultaneously and in one action.

Figure 8D:
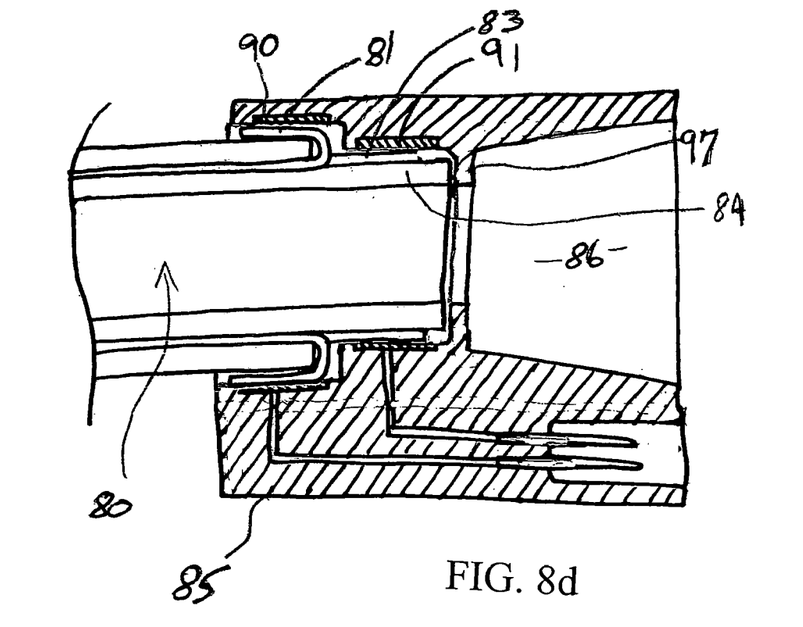
FIG. 8D is a cross sectional elevation view of a terminated conduit incorporating the connector of FIGS. 8B and 8C.

Referring to FIG. 8D the connector 85 is next assembled to the prepared end of conduit 80. This step of assembly comprises sliding the connector 85 onto the end of conduit 80. This brings heating element conductors 83 in contact with ring contact 91 and heating element conductors 81 in contact with ring contact 90. The tube 80 projects into the connector 85 until the forward most end of the inner portion 84 of tube 80 contacts an annular inward protrusion 97. To complete securement of the connector 85 to the conduit 80 a glue or similar adhesive may be injected into the spaces between conduit end 80 and connector 85.

Figure 8E:
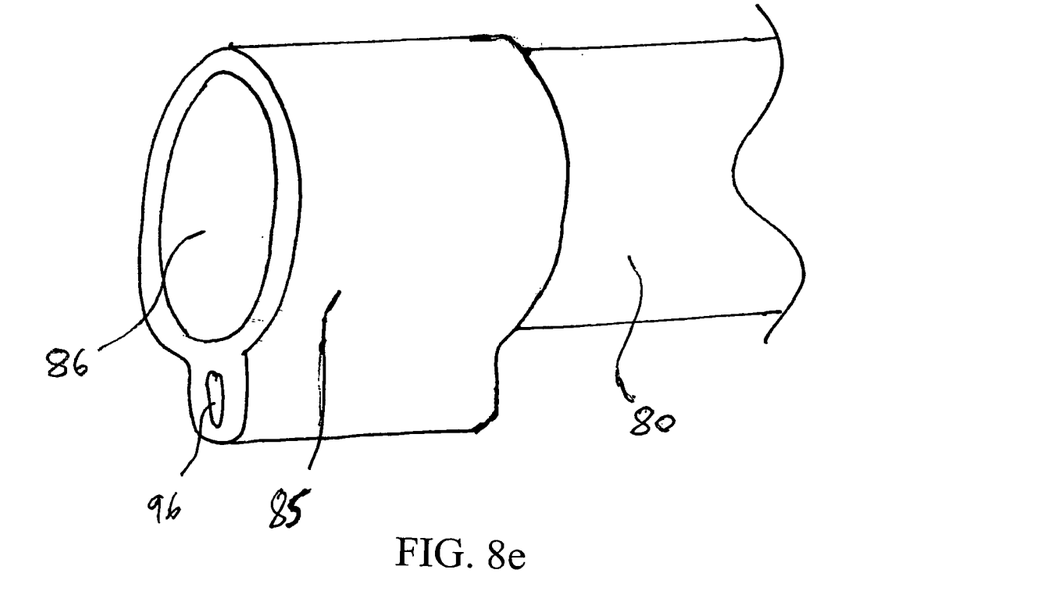
FIG. 8E is a perspective view of the terminated conduit end of FIG. 8D.

A view of the completed terminated conduit end is provided in FIG. 8E.

It is preferred for the present invention that the PTC material is composed to provide a threshold temperature at or just above the preferred gases temperature (eg above the dew-point of the humidified gases) the PTC material will maintain itself at that threshold temperature (with some hysteresis fluctuation) and condensation on the conduit surface will be at least substantially eliminated. This provides more effective condensation control than maintaining an elevated temperature for the humidified gases where condensation may still form on the cold wall surfaces.

PTC material behaviour is exhibited in a range of polymer compositions with electrically conductive fillers. The behaviour can be characterised by a general statement that "providing certain other conditions are fulfilled, the composition becomes electrically conductive when particles of electrically conductive filler form a continuous chain, penetrating the material from the point of entry of electric current to the place where it leaves the polymer material". Polymer compositions containing electrically conductive filler can exhibit PTC properties due to the formation of a chain of filler particles that are close enough for current to flow at a certain temperature, generating heat which increases the temperature of the material until it reaches a phase transformation temperature. At the phase transformation temperature the crystalline polymer matrix changes to an amorphous structure. This change is accompanied by a small thermal expansion, forcing filler particles to move apart, breaking the conductive paths. Accordingly resistance rises sharply at this phase transformation temperature. As the material cools the small thermal conduction allows new conductive paths to form and current flow to resume. The rise and fall in temperature and the thermal contraction and expansion provides an inherent hysteresis in the cycle.

In producing a PTC material a number of factors have a bearing on the performance of the material. Particular factors include the quantity, type and particle size of the carbon black (or other conductive filler) used in the composite, the polymer that the carbon black binds with during mixing of the base materials and the process conditions such as temperature, pressure and time of mixing. It is important that the conductive filler particles are distributed evenly through the composite so that the composite exhibits uniform PTC behaviour.

For the present invention a PTC material having a phase transformation temperature not exceeding 40° C. is desired. One composition meeting these criteria has been developed and has the following composition:

- 20% by weight carbon black powder having a surface area of 254 m$^2$/g and oil Di-Butyl-Phthalate absorption of 188 cm$^3$/100 g. This powder is available as VULCAN XC-72 (powder) from Cabot Corporation.
- 64% Ethylene-Vinyl-Acetate. This material is available as ELVAX (grade 40 w) from Dupont (E.I. du Pont de Nemours and Company), with a density of 965 kg per m$^3$, a melting point of 46° C. and melting index of 52.
- 13.5% Plastomer. An example plastomer is available as EXACT 2M055 from ExxonMobil Corp, having a density of 882 kg/m$^3$, a melting point of 70° C. and a melting index of 3.
- 2.5% Wax.

This material was uniformly mixed and extruded to form a PTC ribbon with embedded conductors using a segmented screw extruder. The composite performance showed an acceptable level of self regulation without the temperature exceeding 40° C.

Varying the amount of carbon black up or down within this composition has the effect of varying the phase transition temperature. Where delivery of humidified gases to a patient a phase transition temperature in the range 30° C. to 45° C. may be appropriate, with the particular transition temperature required depending on the particular humidified gases treatment to be delivered. For example humidified gases delivery is being promoted for the treatment of chronic obstructive pulmonary disease (COPD). Whereas treatment humidified gases are delivered to the patient, usually via a nasal cannular, at between 35 and 45° C. Therefore for treatment of COPD a PTC material having a phase transition temperature in the range 35° C. to 45° C. is preferred. Similarly humidified gases are being promoted for use in patient insufflation for surgical procedures. In this application humidified gases are delivered at a temperature between 35° C. and 40° C. and accordingly a PTC material having a phase transition temperature in this range is preferred. This is also the preferred range for the temperature of humidified gases for respiration of an intubated patient, and therefore the preferred phase transition temperature for the PTC material used in manufacturing a conduit for that purpose. However where a patient is receiving humidified respiratory gases via a face mask it has been found that a somewhat lower delivery temperature is preferable, in the range 30° C. to 35° C. Accordingly for the manufacture of conduits for delivery of respiratory gases to a patient via a face mask a PTC material phase transition temperature of 30° C. to 35° C. is preferred.

It will be appreciated the present invention provides a gases conduit for delivering humidified gases to a patient which may be formed by extrusion, it includes heating in some form to prevent or minimise the formation of condensation. The conduit may include profile features which prevent occlusion by crushing or bending. The conduit includes PTC heating elements of various forms.

What is claimed is:

1. A gases delivery conduit for the supply of humidified medical gases, said conduit comprising:
    an extruded plastic tube useful for the supply of humidified medical gases to a patient, and
    at least one healing element embedded within the wall of the tube to be partially or wholly contained within said wall, said heater element including a pair of electrical conductors separated by a positive temperature coefficient ("PTC") material wherein the localised resistance of said material is positively related to the localised temperature, said positive temperature coefficient ("PTC") material having a phase transformation temperature between 28° C. and 45° C.

2. A conduit as claimed in claim 1 wherein the cross sectional profile of said extruded plastic tube includes inwardly extending ribs on its inner surface, such that total collapse or total occlusion is not possible during bending.

3. A conduit as claimed in claim 2 wherein the heating element is embedded within the inwardly extending internal ribs of the tube.

4. A conduit as claimed in claim 1 wherein said heating element is an elongate flattened tape at least as long as the tube, and having a width and a thickness, with said width being greater than said thickness.

5. A conduit as claimed in claim 4 wherein said tape includes a said conductor disposed along each of a pair of side edges, with a web of said PTC material spanning between said conductors.

6. A conduit as claimed in claim 4 wherein said tape includes an elongate flattened ribbon of said PTC material with a first face and a second face, a said conductor is distributed over said first face, and another said conductor is distributed over said second face.

7. A conduit as claimed in claim 1 wherein the heating element is spiralled within the tube wall.

8. A conduit as claimed in claim 3 wherein said heating element is an elongate flattened tape at least as long as the tube, and having a width and a thickness, with said width being greater than said thickness.

9. A conduit as claimed in any one of claims 1 to 8 including a connector at each end, at least one said connector having one or more electrical contacts contacting and connecting with one or more of the conductors of said heating elements, said connector having an external connection interface and an electrical connection between each said contact and said external connection interface.

10. A conduit as claimed in claim 9 wherein a said connector has a first said electrical contact contacting and connecting with a first said conductor of each said embedded heating element, and a second said electrical contact contacting and connecting with a second conductor of each said heating element, said first contact and first conductors electrically insulated from said second contact and second conductors apart from through said PTC material.

11. A conduit as claimed in claim 10 wherein said connector with said external connection interface has a gases port configured to make a connection with a mating gases port in a first direction, and said connection interface is configured to make connection with a mating connection interface also in said first direction.

12. A method of manufacturing a conduit for the supply of humidified medical gases comprising:
    preparing at least one elongate heating element including a pair of electrical conductors separated by a positive temperature coefficient ("PTC") material wherein the localised resistance of said material is positively related to the localised temperature, said positive temperature coefficient ("PTC") material having a phase transformation temperature between 28° C. and 45° C.
    extruding a plastic tube and simultaneously drawing said heating element into the melt of the extruded tube such that the element is embedded within the wall of the tube and captured as the melt solidifies.

13. A method as claimed in claim 12 including spiralling the heating elements within the tube wall by twisting the extruded tube during forming.

14. A method as claimed in claim in claim 12 including moving the points where the heating elements enter the melt of the extruded tube to spiral or braid the heating elements within the tube wall.

15. A method as claimed in claim 12 including, in a continuous process:
    extruding an inner tube layer,
    applying said elongate healing element to an outer face of said inner tube layer, and
    extruding an over tube layer over said inner tube layer to encapsulate said elongate heating element between said inner layer and said outer layer.

16. A method as claimed in claim 12 including the further steps of:
    (a) removing tube material to exposed conductors of the heating elements; and
    (b) sliding a connector over the trimmed and untrimmed section of the conduit to completely cover the exposed conductors, said connector including at least one electrical contact on its inner surface, which thereby comes into contact with said exposed conductors.

17. A method as claimed in claim 16 including, between steps (a) and (b), the further step of:
    bending back one of the exposed conductors of said heating element over the untrimmed section of said tube;
    and wherein at step (b) said connector includes at least a pair of contacts on its inner surface, with a said contact arranged to contact the bent back conductor of said heating element and another said contact arranged to contact the other conductor of said heating element.

18. A method of terminating an extruded plastic tube with an embedded heating element, the heating element including a pair of electrical conductors separated by a positive temperature coefficient ("PTC") material wherein the localised resistance of said material is positively related to the localised temperature, the method comprising the steps of:
    (a) removing tube material to expose conductors of the heating element, and
    (b) sliding a connector over the trimmed and untrimmed section of the conduit to completely cover the exposed conductors, said connector including at least one electrical contact on its inner surface, which thereby come into contact with said exposed conductors.

19. A method as claimed in claim 18 including, between steps (a) and (b), the further step of:
    bending back one of the exposed conductors of said heating element over the untrimmed section of said tube;
    and wherein at step (b) said connector includes at least a pair of contacts on its inner surface, with a said contact arranged to contact the bent back conductor of said heating element and another said contact arranged to contact the other conductor of said heating element.

* * * * *